(12) United States Patent
Searfoss et al.

(10) Patent No.: US 8,974,420 B2
(45) Date of Patent: Mar. 10, 2015

(54) LARGE FRENCH SIZE HEMOSTATIC VALVE CONFIGURATION

(75) Inventors: Timothy A. Searfoss, New Port Richey, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 364 days.

(21) Appl. No.: 13/619,492

(22) Filed: Sep. 14, 2012

(65) Prior Publication Data

US 2013/0072956 A1    Mar. 21, 2013

Related U.S. Application Data

(60) Provisional application No. 61/535,485, filed on Sep. 16, 2011.

(51) Int. Cl.
*A61M 39/06*    (2006.01)

(52) U.S. Cl.
CPC .................. *A61M 39/0606* (2013.01)
USPC ........ 604/167.04; 604/256; 606/108; 137/849

(58) Field of Classification Search
CPC .......................... A61M 39/06; A61M 2039/064
USPC ........ 606/108, 184, 185; 604/167.03, 167.04, 604/256; 137/512.15, 512.5, 846, 849
See application file for complete search history.

(56) References Cited

U.S. PATENT DOCUMENTS

| | | |
|---|---|---|
| 4,610,665 A | 9/1986 | Matsumoto et al. |
| 4,626,245 A | 12/1986 | Weinstein |
| 4,798,594 A | 1/1989 | Hillstead |
| 4,895,565 A | 1/1990 | Hillstead |
| 4,960,412 A | 10/1990 | Fink |
| 5,000,745 A | 3/1991 | Guest et al. |
| 5,041,095 A | 8/1991 | Littrell |
| 5,102,395 A | 4/1992 | Cheer et al. |
| 5,125,904 A | 6/1992 | Lee |
| 5,176,652 A | 1/1993 | Littrell |
| 5,267,966 A | 12/1993 | Paul |
| 5,304,156 A | 4/1994 | Sylvanowicz et al. |
| 5,409,463 A | 4/1995 | Thomas et al. |
| 5,520,655 A | 5/1996 | Davila et al. |
| 5,538,505 A | 7/1996 | Weinstein et al. |
| 5,562,632 A | 10/1996 | Davila et al. |
| 5,702,370 A | 12/1997 | Sylvanowicz et al. |
| 6,159,182 A | 12/2000 | Davis et al. |
| 6,663,599 B2 | 12/2003 | Osbourne et al. |
| 7,621,894 B2 | 11/2009 | Leeflang et al. |

(Continued)

*Primary Examiner* — Kathleen Holwerda
(74) *Attorney, Agent, or Firm* — Locke Lord LLP; Scott D. Wofsy; Joshua L. Jones (57) ABSTRACT

A hemostasis valve for a vascular introducer includes a valve body having a seal region with opposed substantially planar proximal and distal end surfaces and a central axis extending through the seal region perpendicular to the proximal and distal end surfaces. The seal region has a first grouping of circumferentially arranged and equidistantly spaced linear cuts extending radially outward from the central axis, and through the seal region from the proximal end surface to the distal end surface. The seal region has a second grouping of circumferentially arranged and equidistantly spaced linear cuts in the distal end surface extending tangentially outward from the first grouping of linear cuts, and partially from the distal end surface to a depth short of the proximal end surface to facilitate passage of a variety of sizes of medical devices through the seal region.

21 Claims, 6 Drawing Sheets

(56) References Cited

U.S. PATENT DOCUMENTS

| | | |
|---|---|---|
| 7,901,379 B2 | 3/2011 | Argentine et al. |
| 8,123,726 B2 | 2/2012 | Searfoss et al. |
| 8,262,671 B2 | 9/2012 | Osypka |
| 2004/0210194 A1 | 10/2004 | Bonnette et al. |
| 2005/0267487 A1 | 12/2005 | Christensen et al. |
| 2006/0149294 A1 | 7/2006 | Argentine et al. |
| 2009/0143739 A1 | 6/2009 | Nardeo et al. |
| 2010/0185153 A1 | 7/2010 | Sugiki et al. |
| 2010/0193516 A1* | 8/2010 | LaBean et al. .......... 220/229 |
| 2010/0204655 A1 | 8/2010 | Melsheimer |

\* cited by examiner

LARGE FRENCH SIZE HEMOSTATIC VALVE CONFIGURATION

CROSS-REFERENCE TO RELATED APPLICATIONS

This application claims the benefit of priority to U.S. Provisional Patent Application No. 61/535,485, filed Sep. 16, 2011, which is incorporated by reference herein in its entirety.

BACKGROUND OF THE INVENTION

1. Field of the Invention

The subject invention is directed to a hemostasis valve for vascular introducers that provides a complete hemostatic seal regardless of the diameter of the object introduced through the valve, while exhibiting lower insertion and extraction forces than prior-art hemostasis valves.

2. Description of Related Art

The percutaneous introduction of diagnostic and therapeutic devices such as pacemaker leads and cardiovascular catheters into a blood vessel is typically accomplished with the aid of an introducer assembly. Introducer assemblies generally include a dilator having a tapered end portion and a thin-walled introducer sheath having a lumen extending through the sheath to initially accommodate the dilator, and subsequently accommodate the passage of a pacemaker lead or catheter.

Typically, the percutaneous introduction of an introducer assembly is accomplished by first inserting a needle into the blood vessel at a desired location and verifying its position by observing fluid return or by a similar method. While the needle is held firmly in place, a guidewire is inserted through the needle cannula to the desired depth. The guidewire is then held in place and the needle is withdrawn. Pressure is applied on the puncture site to minimize blood loss. Next, the introducer assembly is threaded over the guidewire. The introducer assembly is grasped close to the skin surface and advanced through the tissue to the desired position. Then, the dilator and guidewire are removed, leaving the sheath installed. A lead, catheter, or similar diagnostic or therapeutic device is then introduced into the sheath and advanced to the desired position. Lastly, the sheath is removed, leaving the device disposed within the blood vessel.

It is known to configure an introducer sheath so that it may be easily removed or separated from the lead or catheter after it has been put in place. For example, it is known to provide score lines in the wall of the sheath to enable the sheath to be peeled away, slit, or split open. Once the sheath has been removed and the catheter has been put in place, therapeutic medical devices such as endocardial pacing/defibrillation leads may be introduced into the blood vessel through the catheter.

Once the sheath has been inserted into a blood vessel, it provides a passage for the free flow of blood, which may result in significant blood loss from a patient. The sheath also provides an open passage for the introduction of air into the blood vessel, which may cause an embolism in the vascular system of the patient. To overcome these problems, vascular introducers have been developed with hemostatic valves that prevent the free flow of blood through the introducer sheath.

In such prior art devices, the hemostatic valve is configured to create frictional resistance to the passage of therapeutic devices such as flexible cardiac leads. This makes introduction of a lead difficult and can actually cause damage to the lead.

The prior art hemostasis valve designs are not capable of providing an effective hemostatic seal on introduced medical devices having a very wide range of French sizes, and are especially challenged when presented with larger French size devices (e.g. larger than 12F), because such designs use radially aligned slits that form triangular gaps at the slit intersections, which leak blood and/or fluid upon insertion of a medical device. Additionally, such prior art hemostasis valve designs are not capable of sealing a wide variety of French sizes, while still maintaining the ability to break and peel away after use.

There has also been a dramatic increase in the number and types of new medical devices that have large French sizes (e.g. larger than 12F) followed by smaller French sizes (e.g. smaller than 12F) on the same unit. Such combinatorial medical device units pose a challenge that exceeds the capabilities of prior art hemostasis valve designs. Additionally, such prior art hemostasis valve designs are not able to provide effective hemostatic seals when more than one medical device is introduced through the hemostasis valve simultaneously.

There is an urgent need for a hemostasis valve for a vascular introducer that effectively prevents the backflow of blood and other fluids, while accommodating: insertion of medical devices with a wide range of French sizes, insertion of medical devices with combinatorial units of differing French sizes, and/or insertion of multiple medical devices at the same time.

SUMMARY OF THE INVENTION

A hemostasis valve for a vascular introducer is disclosed which includes a valve body with a seal region having substantially planar proximal and distal end surfaces and defining a central axis extending through the seal region substantially perpendicular to the proximal and distal end surfaces. A first grouping of linear cuts is defined in the seal region extending radially outward from the central axis for sealed passage of medical devices through the seal region. A second grouping of linear cuts is defined in the seal region extending tangentially outward from terminal ends of respective linear cuts within the first grouping of linear cuts. The first grouping of linear cuts extends through the seal region from the proximal end surface to the distal end surface. The second grouping of linear cuts only extends partially from the distal end surface to a depth short of the proximal end surface to facilitate sealed passage of a variety of sizes of medical devices through the seal region.

In exemplary embodiments, the linear cuts of the first grouping of linear cuts are circumferentially arranged and equidistantly spaced apart, and the linear cuts of the second grouping of linear cuts are circumferentially arranged and equidistantly spaced apart. The first and second groupings of linear cuts can contain equal numbers of linear cuts. For example, the first grouping of linear cuts can include 4 to 12 linear cuts and the second grouping of linear cuts can include the same number of linear cuts.

In certain embodiments, each of the linear cuts in the first grouping of linear cuts protrudes through the seal region at an angle of rotation relative to the central axis. The angle of rotation can be from about 30 degrees to about 90 degrees, or any other suitable angle. For example, the angle of rotation can be about 45 degrees.

In another aspect, the linear cuts of the second grouping of linear cuts extend outward at a tangential angle relative to the terminal ends of respective linear cuts within the first grouping of linear cuts. The tangential angle can be from about 90 degrees to about 270 degrees or any other suitable angle. For example, the tangential angle can be about 91 degrees.

In accordance with certain embodiments, the linear cuts of the second grouping of linear cuts can extend partially into the distal end surface at an angle of incision relative to the central axis to a depth short of the proximal end surface leaving a remaining thickness of uncut material adjacent to the proximal end surface. The angle of incision can be from about 5 degrees to about 65 degrees, or any other suitable angle. For example, the angle of incision can be about 22 degrees. The remaining thickness of uncut material adjacent to the proximal end surface can be between about 1% and about 50% of the total thickness of the valve body between proximal and distal end surfaces, or any other suitable percentage. The thickness of uncut material adjacent to the proximal end surface can be between about 0.005 inches and about 0.020 inches, or any other suitable amount for a given application.

The valve body can include fixturing apertures radially outward from the second grouping of linear cuts for securing the valve body within a valve housing. The valve body can be formed from a silicone based material, or any other suitable material or combination of materials. It is contemplated that the silicone based material can have a durometer hardness of between about 20 D and about 35 D.

Additionally, the valve body can further include a pair of planar slits extending outward from two diametrically opposed linear cuts in the second grouping of linear cuts. The pair of planar slits can extend through the valve body from the proximal end surface to the distal end surface. It is also contemplated that the pair of planar slits can extend outwardly from the outer limit of each of the diametrically opposed linear cuts in the second grouping of linear cuts to the outer edge of the valve body.

The invention also includes a method of placing a hemostasis valve as described above into a vascular introducer, e.g. in a patient, and introducing at least one medical device through the hemostasis valve. The method also includes sealing the hemostasis valve to the at least one medical device to prevent efflux of fluid therebetween, e.g. blood or bodily fluid from the patient. The method can include stacking multiple hemostasis valves in one introducer with two or more hemostasis vales stacked adjacent to each other.

These and other features of the hemostasis valve of the subject invention will become more readily apparent to those having ordinary skill in the art from the following detailed description of the invention taken in conjunction with the several drawings figures.

BRIEF DESCRIPTION OF THE DRAWINGS

So that those skilled in the art to which the subject invention belongs will readily understand how to make and use the hemostasis valve of the subject invention without undue experimentation, preferred embodiments of the hemostasis valve will be described in detail below with reference to certain figures, wherein.

DETAILED DESCRIPTION

Figure 1:
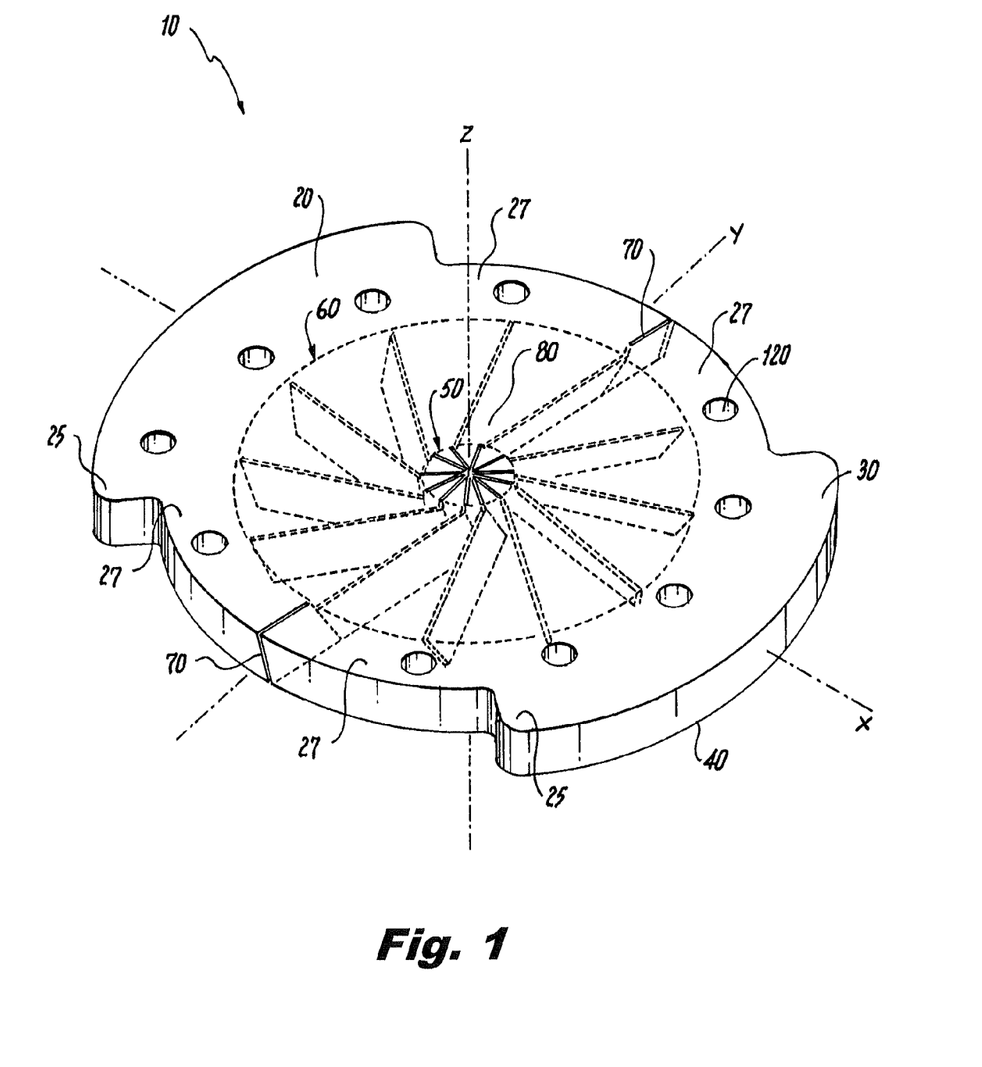
FIG. 1 is a perspective view of the hemostasis valve of the subject invention, illustrating the proximal end surface of the valve.

Referring now to the drawings wherein like reference numerals identify similar structural features or aspects of the medical devices disclosed herein, there is illustrated in FIG. 1 an exemplary embodiment of a novel hemostasis valve member of the invention designated generally by reference numeral 10.

An exemplary vascular introducer is disclosed in U.S. Patent Application Publications 2008/0097386 and 2010/0312190, both of which are incorporated herein by reference in their entirety for purposes of enablement and illustration. Those skilled in the art will readily appreciate that the disclosure of vascular introducer 10 should not be construed as limiting the scope of the subject invention in any way. In other words, while the hemostasis valve of the subject invention can certainly be employed with the exemplary vascular introducer of, for example, U.S. Patent Application Publication 2010/0312190, it can also be employed with other types of vascular introducers, including those which are not designed to be split in half or peeled away, as well as other types of medical devices, such as cannulae or trocars in which a hemostatic valve may be employed to prevent the backflow of blood and other fluids.

FIG. 1 illustrates an exemplary embodiment of a hemostasis valve member of the present invention, designated generally by the reference numeral 10. As shown, hemostasis valve member 10 includes valve body 20 with a substantially planar proximal end surface 30 and a substantially planar distal end surface 40. In the exemplary embodiment shown, valve body 20 is generally cylindrical in shape, with proximal end surface 30 and distal end surface 40 being positioned substantially parallel to one another and spaced apart by a predetermined distance, i.e., thickness. Valve body 20 includes a generally cylindrical and centrally located seal region 80. In the exemplary embodiment shown, seal region 80 is centered at the perpendicular intersection of lateral axis x and lateral axis y, which are parallel to proximal end surface 30 and distal end surface 40, and span the diameter of valve body 20. Axis z extends through the center of valve body 20 and is perpendicular to proximal end surface 30 and distal end surface 40, as well as lateral axis x and lateral axis y.

As shown in FIG. 1, distal end surface 40 of seal region 80 may include a plurality of linear cuts formed on the surface. In one embodiment, distal end surface 40 includes a first grouping of circumferentially arranged and equidistantly spaced apart linear cuts 50, which extends radially outward from the center of seal region 80. Distal end surface 40 also includes a second grouping of circumferentially arranged and equidistantly spaced apart linear cuts 60, which extends tangentially outward from the terminal ends of respective linear cuts within the first grouping of linear cuts 50. The second grouping of linear cuts 60 functions to distribute the stretching of the material of valve body 20 to conform to the size and shape of the medical device introduced through seal region 80, facilitating use of a variety of sizes of medical devices. In this regard, the multiplicity of linear cuts in the second grouping of linear cuts 60, combined with the increased length of these linear cuts that results from their tangential, outward extension from the terminal ends of respective linear cuts within the first grouping of linear cuts, provides the requisite degree of elasticity (i.e. stretching) to allow low insertion force with no premature breakage of valve body 20. In the exemplary embodiment shown, the first grouping of linear cuts 50 and the second grouping of linear cuts 60 each contain equal numbers of linear cuts of equal length. In a preferred embodiment, the first and second groupings of linear cuts contain twelve linear cuts of equal length. Additionally, valve body 20 contains a pair of planar slits 70 extending radially outward from the outer end of two diametrically opposed linear cuts in the second grouping of linear cuts 60 that are generally parallel to lateral axis y.

In addition, fixturing apertures 120 for securing valve body 20 within the actuation cap, or another portion of a similar vascular introducer, are formed in mating region 27, which is located between the outer limit of the second grouping of linear cuts 60 and the peripheral edge of valve body 20. Mating region 27 of valve body 20 facilitates mating of hemostasis valve member 10 with a mating seal ring in the vascular introducer, or similar medical device. Additionally, hemostasis valve member 10 may optionally contain opposing mounting sections 25 that protrude from valve body 20 parallel to lateral axis x for seating and/or securing valve body 20 within a vascular introducer, or similar medical device.

Figure 2:
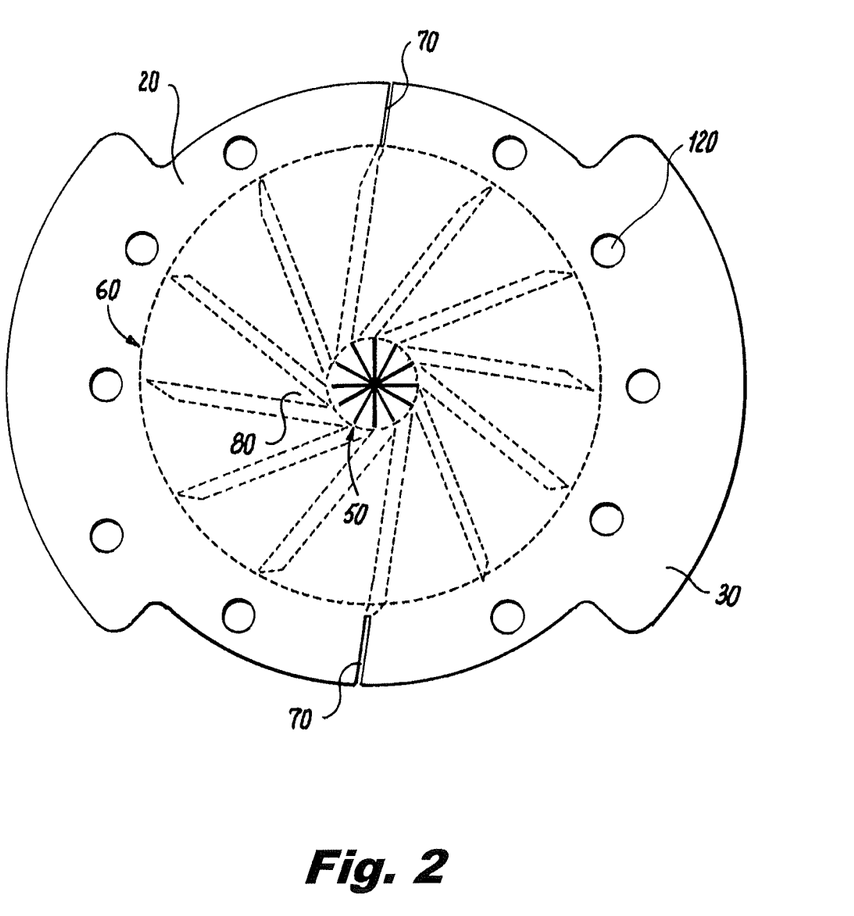
FIG. 2 is a plan view of the hemostasis valve of the subject invention, illustrating the proximal end surface of the valve.

Referring now to FIG. 2, a detailed view of proximal end surface 30 of hemostasis valve 10 shows that the first grouping of linear cuts 50 in distal end surface 40 extends through seal region 80 to proximal end surface 30. However, the second grouping of linear cuts 60 in distal end surface 40 extends partially, but not completely, through seal region 80 to a depth adjacent to the proximal end surface 30. Additionally, the pair of planar slits 70 in distal end surface 40 extends through valve body 20 to proximal end surface 30.

Figure 3:
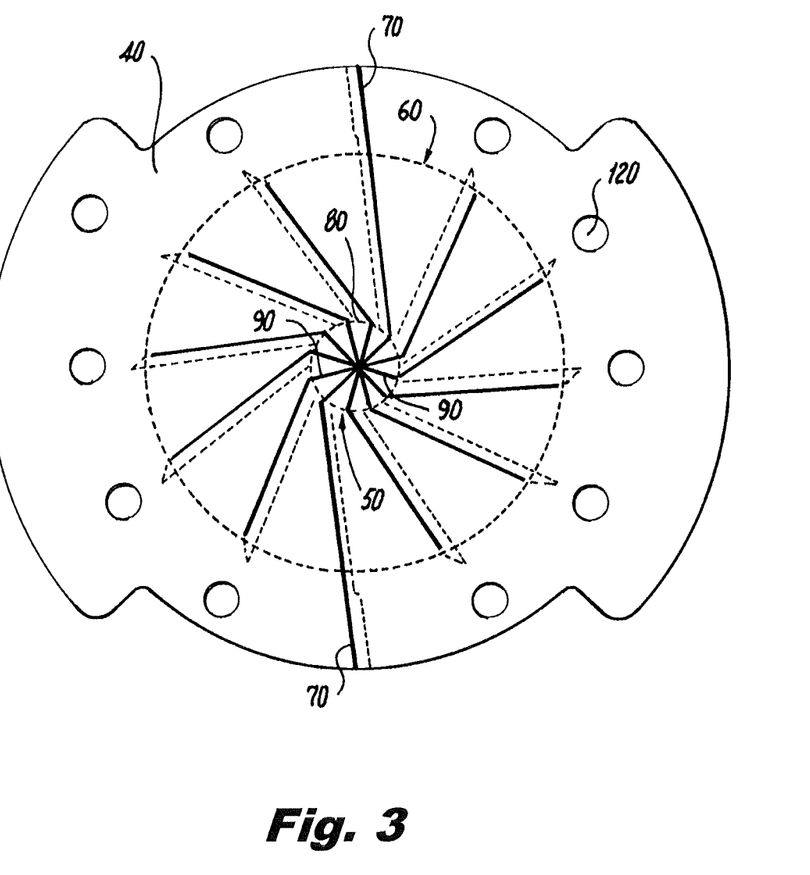
FIG. 3 is a plan view of the hemostasis valve of the subject invention, illustrating the distal end surface of the valve.

As shown in FIG. 3, in an exemplary embodiment of the hemostasis valve 10, the second grouping of linear cuts 60 in distal end surface 40 extend tangentially outward from the terminal ends of respective linear cuts within the first grouping of linear cuts 50 at tangent angle 90. In the exemplary embodiment shown, each of the twelve linear cuts in the second grouping of linear cuts 60 extends tangentially outward from the terminal end of one of the twelve linear cuts in the first grouping of linear cuts 50 at a tangential angle 90 that is equal to about 91 degrees. It is contemplated within the scope of the invention that tangential angle 90 may vary from about 90 degrees to about 270 degrees. In preferred embodiments, tangent angle 90 may vary from about 90 degrees to about 170 degrees.

Figure 4:
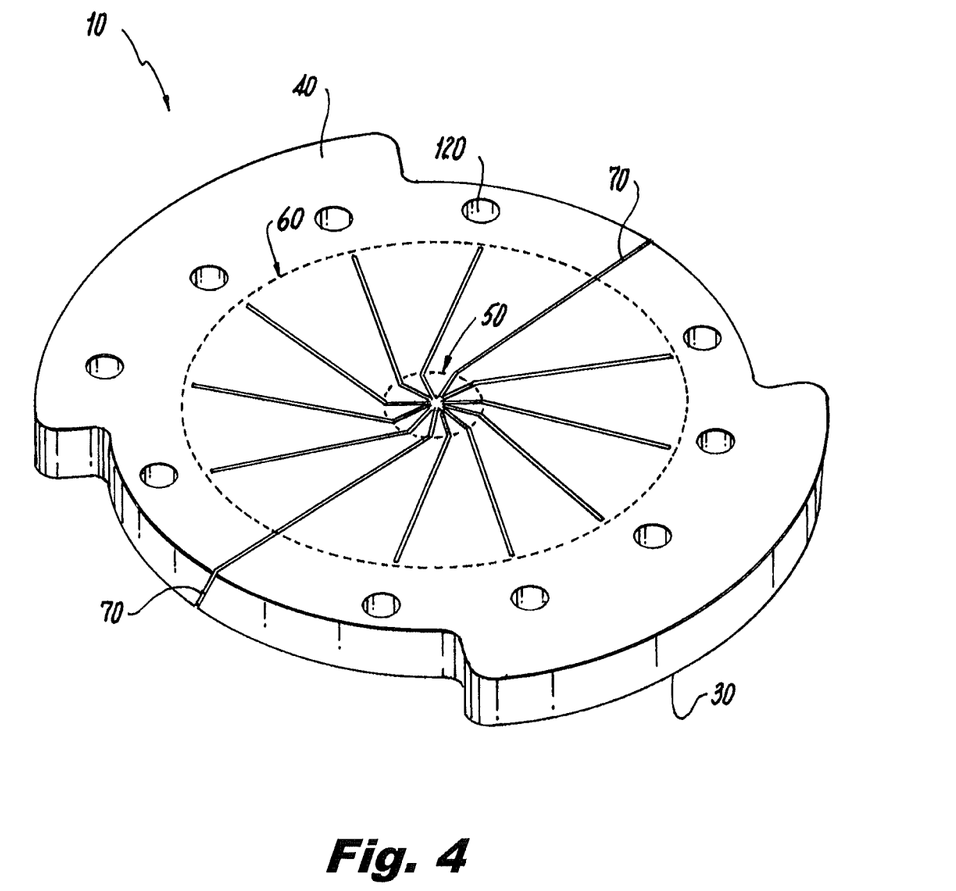
FIG. 4 is a perspective view of the hemostasis valve of the subject invention, illustrating the first and second groupings of linear cuts, as well as the pair of planar slits, as viewed from the distal end surface.

With reference now to FIG. 4, a perspective view of hemostasis, valve 10, similar to FIG. 1 but without the internal features, shows only the surface features to illustrate the first grouping of linear cuts 50, as well as the pair of planar slits 70, as viewed toward the distal end surface 40. The second grouping of linear cuts 60 is visible on distal end surface 40, but they do not reach all the way from distal end surface 40 to proximal end surface 30.

Figure 5:
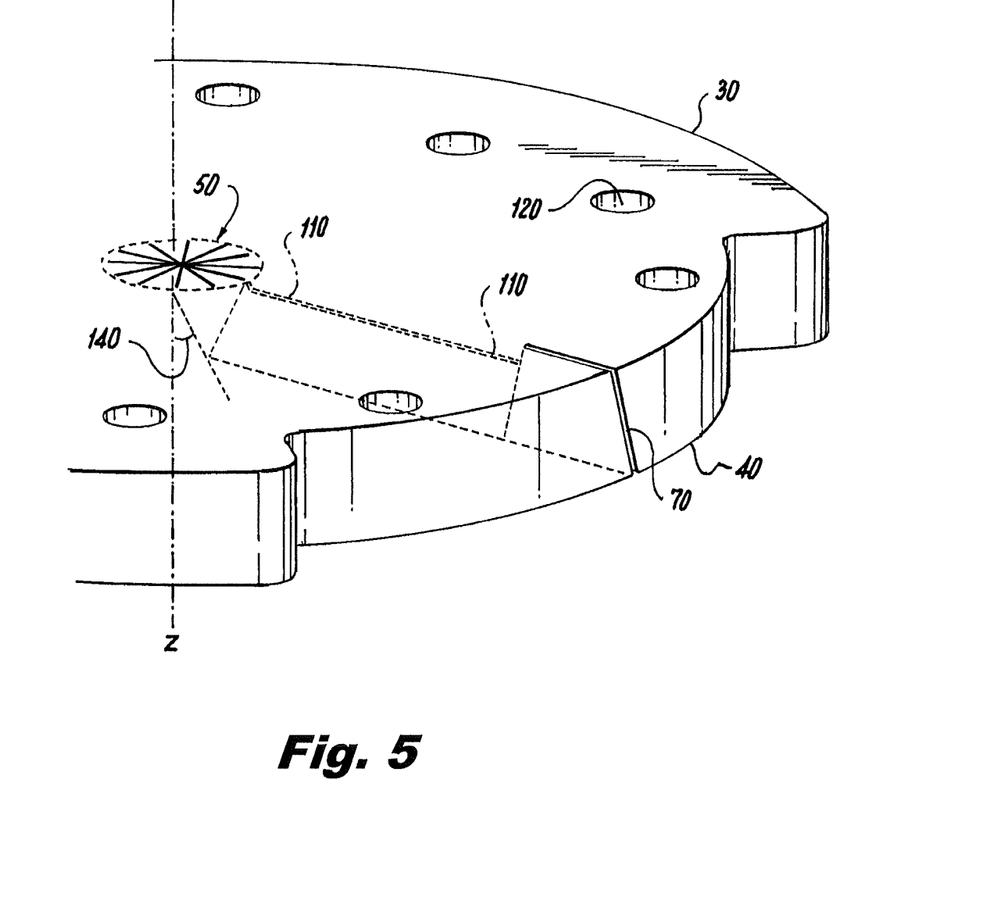
FIG. 5 is a perspective view of the hemostasis valve of the subject invention, illustrating the remaining material in the proximal end surface for a linear indentation in the second grouping of linear cuts.

Referring now to FIG. 5, a partial perspective view of hemostasis valve 10 shows that linear cuts within the first grouping of linear cuts 50 protrude through seal region 80 at an angle of rotation 140 relative to axis z. In the illustrative embodiment shown, angle of rotation 140 is about 45 degrees relative to central axis z. However, it is contemplated within the scope of the invention that angle of rotation 140 may vary from about 30 degrees to about 90 degrees relative to central axis z. Additionally, FIG. 5 shows that linear cuts within the second grouping of linear cuts 60, which extend partially into distal end surface 40, leave a remaining thickness of uncut material 110 adjacent to proximal end surface 30. The thickness of the remaining uncut material may be any suitable thickness that will provide a balance between valve body 20 not tearing prematurely during insertion of the largest French size devices (e.g. larger than 12F), and tearing at an acceptable force during the break and peel of hemostasis valve 10 upon completion of the procedure. For example, the remaining thickness of uncut material 110 can be between about 1% and about 50% of the total thickness of the valve body, and the remaining thickness of uncut material 110 can be between about 0.005 inches and about 0.020 inches.

Figure 6:
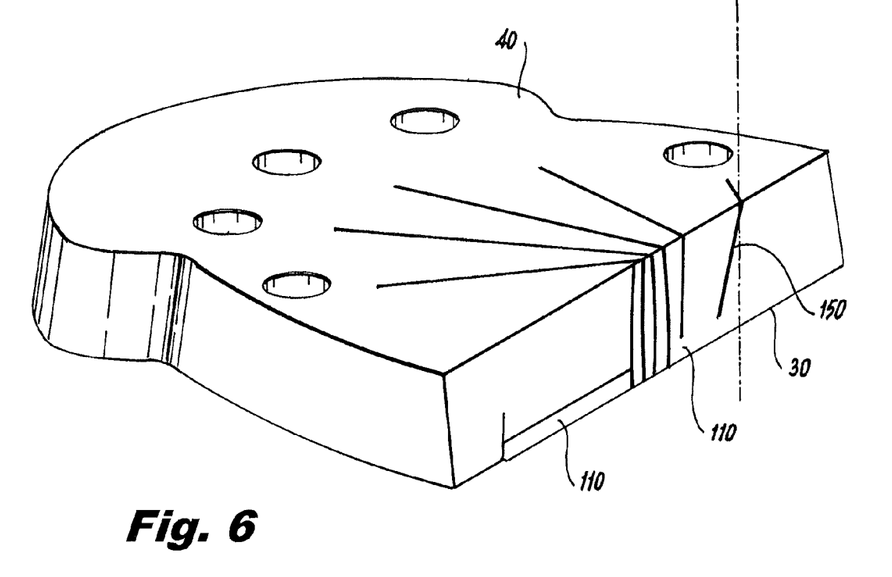
FIG. 6 is a partial cross-sectional view of the hemostasis valve of the subject invention taken along the left side breakaway line, illustrating the angle of incision of the linear cuts of the second grouping of linear cuts, with the distal end surface facing up.

With reference now to FIG. 6, a partial cross-sectional view of hemostasis valve 10 shows the remaining thickness of uncut material 110 left on proximal end surface 30 for exemplary linear cuts within the second grouping of linear cuts 60. Additionally, linear cuts within the second grouping of twelve linear cuts 60 are angularly offset from the central axis z such that they have an angle of incision 150 relative to central axis z. In the exemplary embodiment shown, angle of incision 150 is about 22 degrees relative to axis z.

Figure 7:
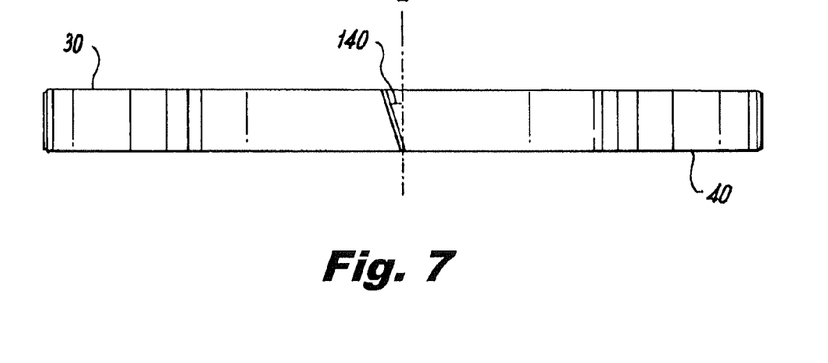
FIG. 7 is a side view of the hemostasis valve of the subject invention, illustrating the angle of rotation of the linear cuts in the first grouping of linear cuts.

Referring to FIG. 7, a side view of the hemostasis valve 10 shows the angle of rotation 140 for one of the exemplary linear cuts within the first grouping of linear cuts 50. Valve body 20 is preferably formed from a silicone based polymeric material of a softer durometer hardness (e.g. about 20 D to about 35 D). It is envisioned that the silicone based polymeric material can include a filler. For example, the valve body 10 can be formed from a silicone matrix consisting of about 20 to 35 durometer silicone or a similar material, with a mixture of less than about 5% titanium dioxide or a similar material as a filler. The function of the valve is not dependant on the selection of a filler.

While shown and described above in the exemplary context of having twelve linear cuts in each of the first and second groupings of linear cuts, those skilled in the art will readily appreciate that any suitable number of linear cuts can be used without departing from the spirit and scope of the invention. For example, there can be between 4 to 12 linear cuts in the first grouping, and the same number of linear cuts in the second grouping. Also, while shown and described in the exemplary context of using a single hemostasis valve with an introducer, those skilled in the art will readily appreciate that multiple hemostasis valves can be stacked in one introducer, for example two or more hemostasis valves can be stacked adjacent to one another in a single introducer, without departing from the spirit and scope of the invention.

The embodiments of the valve member described above are exemplary and do not limit the invention in any way. Relative terms such as "proximal," "distal," "inner," "outer", and "terminal" have been included for ease of description only, and should not be interpreted as limiting the invention. Those skilled in the art will readily appreciate that many changes may be made to the described embodiments without departing from the scope of the subject invention as defined by the appended claims.

What is claimed is:
1. A hemostasis valve for a vascular introducer comprising:
a valve body including a seal region having substantially planar proximal and distal end surfaces and defining a central axis extending through the seal region substantially perpendicular to the proximal and distal end surfaces;

a first grouping of linear cuts defined in the seal region extending radially outward from the central axis for sealed passage of medical devices through the seal region; and a second grouping of linear cuts defined in the seal region extending tangentially outward from terminal ends of respective linear cuts within the first grouping of linear cuts, wherein the first grouping of linear cuts extends through the seal region from the proximal end surface to the distal end surface, and wherein the second grouping of linear cuts extends partially from the distal end surface to a depth short of the proximal end surface to facilitate sealed passage of a variety of sizes of medical devices through the seal region.

2. The hemostasis valve of claim 1, wherein the first grouping of linear cuts are circumferentially arranged and equidistantly spaced, the second grouping of linear cuts are circumferentially arranged and equidistantly spaced, and the first and second groupings of linear cuts contain equal numbers of linear cuts.

3. The hemostasis valve of claim 1, wherein the first grouping of linear cuts includes 4 to 12 linear cuts and the second grouping of linear cuts includes the same number of linear cuts as the first grouping.

4. The hemostasis valve of claim 1, wherein the linear cuts in the first grouping of linear cuts protrude through the seal region at an angle of rotation relative to the central axis.

5. The hemostasis valve of claim 4, wherein the angle of rotation is from about 30 degrees to about 90 degrees.

6. The hemostasis valve of claim 4, wherein the angle of rotation is about 45 degrees.

7. The hemostasis valve of claim 1, wherein the linear cuts of the second grouping of linear cuts extend outward at a tangential angle relative to terminal ends of respective linear cuts of the first grouping of linear cuts.

8. The hemostasis valve of claim 7, wherein the tangential angle is from about 90 degrees to about 270 degrees.

9. The hemostasis valve of claim 7, wherein the tangential angle is about 91 degrees.

10. The hemostasis valve of claim 1, wherein the linear cuts of the second grouping of linear cuts extend partially from the distal end surface at an angle of incision relative to the central axis to a depth short of the proximal end surface leaving a remaining thickness of uncut material adjacent to the proximal end surface.

11. The hemostasis valve of claim 10, wherein the angle of incision is from about 5 degrees to about 65 degrees.

12. The hemostasis valve of claim 10, wherein the angle of incision is about 22 degrees.

13. The hemostasis valve of claim 10, wherein the remaining thickness of uncut material adjacent to the proximal end surface is between about 1% and about 50% of the total thickness of the valve body between the proximal and distal end surfaces.

14. The hemostasis valve of claim 10, wherein the remaining thickness of uncut material adjacent to the proximal end surface is between about 0.005 inches and about 0.020 inches.

15. The hemostasis valve of claim 1, wherein the valve body includes fixturing apertures radially outward from the second grouping of linear cuts for securing the valve body within a valve housing.

16. The hemostasis valve of claim 1, wherein the valve body includes a silicone based material.

17. The hemostasis valve of claim 16, wherein the silicone based material has a durometer hardness of between about 20D and about 35D.

18. The hemostasis valve of claim 1, wherein the valve body defines a pair of planar slits extending outward from two diametrically opposed linear cuts in the second grouping of linear cuts, wherein the pair of planar slits extends through the valve body from the proximal end surface to the distal end surface.

19. The hemostasis valve of claim 18, wherein the pair of planar slits extends outwardly from the outer limit of each of the diametrically opposed linear cuts in the second grouping of linear cuts to an outer edge of the valve body.

20. A method comprising:

placing a hemostasis valve as recited in claim 1 into a vascular introducer;

introducing at least one medical device through the hemostasis valve; and sealing the hemostasis valve to the at least one medical device to prevent efflux of fluid therebetween.

21. A method as recited in claim 20, further comprising stacking multiple hemostasis valves in one introducer with two or more hemostasis valves stacked adjacent to each other.

* * * * *